(12) United States Patent
Berberich et al.

(10) Patent No.: US 11,719,614 B2
(45) Date of Patent: Aug. 8, 2023

(54) METHOD FOR ANALYZING THE PARTICLES CONTAINED IN AN OPERATING FLUID OF AN APPARATUS, AND APPARATUS FOR CARRYING OUT THE METHOD

(71) Applicant: Bayerische Motoren Werke Aktiengesellschaft, Munich (DE)

(72) Inventors: Niklas Berberich, Munich (DE); Dominik Huber, Garching bei Muenchen (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 248 days.

(21) Appl. No.: 17/041,376

(22) PCT Filed: Apr. 17, 2019

(86) PCT No.: PCT/EP2019/059982
§ 371 (c)(1),
(2) Date: Sep. 24, 2020

(87) PCT Pub. No.: WO2019/219323
PCT Pub. Date: Nov. 21, 2019

(65) Prior Publication Data
US 2021/0116351 A1 Apr. 22, 2021

(30) Foreign Application Priority Data
May 15, 2018 (DE) .................. 10 2018 207 441.0

(51) Int. Cl.
*G01N 15/06* (2006.01)
*G01N 33/28* (2006.01)
*G01N 1/20* (2006.01)

(52) U.S. Cl.
CPC ..... *G01N 15/0618* (2013.01); *G01N 15/0656* (2013.01); *G01N 33/2835* (2013.01); *G01N 2001/2064* (2013.01)

(58) Field of Classification Search
CPC .......... G01N 15/0618; G01N 15/0656; G01N 2001/2064; G01N 33/2835; C02F 1/38;
(Continued)

(56) References Cited

U.S. PATENT DOCUMENTS 3,472,371 A * 10/1969 Ayerst .................. B07B 7/08
209/733
3,981,584 A 9/1976 Guymer
(Continued)

FOREIGN PATENT DOCUMENTS

CN 101925810 A 12/2010
DE 10 2009 011 846 B4 9/2010
(Continued)

OTHER PUBLICATIONS

Chinese Office Action issued in Chinese application No. 201980019286.9 dated Apr. 21, 2012, with English translation (Fifteen (15) pages).
(Continued)

*Primary Examiner* — Hoa Q Pham
(74) *Attorney, Agent, or Firm* — Crowell & Moring LLP

(57) ABSTRACT

A method of analyzing particles present in a service fluid of a device includes analyzing the particles during operation of the device where a service fluid flows through a service fluid circuit of the device during the analyzing. The method further includes branching off a service fluid stream at a first branch point of the service fluid circuit, feeding the branched-off service fluid stream to a separation unit, branching the branched-off service fluid stream into a first service fluid stream and a second service fluid stream by the
(Continued)

separation unit, feeding a majority of particles present in the branched-off service fluid stream to the first service fluid stream by the separation unit, and ascertaining at least one parameter of the particles fed to the first service fluid stream by an evaluation unit.

14 Claims, 1 Drawing Sheet

(58) Field of Classification Search
CPC ............ C02F 2209/105; B01D 21/267; B01D 17/0217
USPC .......................................... 356/335–343, 73
See application file for complete search history.

(56) References Cited

U.S. PATENT DOCUMENTS

| | | | |
|---|---|---|---|
| 5,028,318 A | 7/1991 | Aslin | |
| 5,560,889 A * | 10/1996 | Ogino | G01N 1/40 |
| | | | 436/178 |
| 5,882,524 A | 3/1999 | Storey et al. | |
| 6,598,464 B1 | 7/2003 | Rossi | |
| 8,708,159 B2 * | 4/2014 | Thanoo | F04F 5/44 |
| | | | 209/712 |
| 8,813,540 B2 | 8/2014 | Dantler | |
| 2009/0211379 A1 | 8/2009 | Reintjes et al. | |
| 2015/0048011 A1 | 2/2015 | Howard et al. | |
| 2016/0370275 A1 | 12/2016 | Weiser | |
| 2022/0250095 A1 * | 8/2022 | Gaddum | C12M 33/10 |

FOREIGN PATENT DOCUMENTS

| | | | |
|---|---|---|---|
| GB | 1415311 A | | 11/1975 |
| JP | 9-138196 A | | 5/1997 |
| JP | 2004340804 A | * | 12/2004 |
| WO | WO 2009/094076 A2 | | 7/2009 |

OTHER PUBLICATIONS

PCT/EP2019/059982, International Search Report dated Jul. 18, 2019 (Two (2) pages).
German-language German Office Action issued in German application No. 10 2018 207 441.0 dated Jan. 30, 2019 (Seven (7) pages).
German-language German Office Action issued in German application No. 10 2018 207 441.0 dated Nov. 16, 2021 (Eight (8) pages).
Chinese Office Action issued in Chinese application No. 201980019286.9 dated Oct. 21, 2022, with English translation (Twenty (20) pages).
Editorial Board of Mechanical (Power) Engineer, "Mechanical (Power) Engineer", China Machine Press, Dec. 31, 1996 (Four (4) total pages)—Japanese-language.
Changwu et al., "Chemical Supervision Technology of Thermal Power Plant", China Electric Power Press, Dec. 31, 2005 (Three (3) total pages).—Japanese-language.

* cited by examiner

METHOD FOR ANALYZING THE PARTICLES CONTAINED IN AN OPERATING FLUID OF AN APPARATUS, AND APPARATUS FOR CARRYING OUT THE METHOD

BACKGROUND AND SUMMARY OF THE INVENTION

The present invention relates to a method of analyzing the particles present in a service fluid of a device, and to a device for performing this method.

Solid particles can get into the motor oil of internal combustion engines, and when these arrive at "running surfaces" of moving engine parts they can lead to mechanical damage to the internal combustion engine. Such solid particles may originate, for example, from the engine manufacturing process or result from abrasion or wear processes.

In the production of internal combustion engines, it is therefore important that it is determined within the scope of quality control whether solid particles are present in the motor oil in a critical amount and/or a critical size.

It is an object of the invention to specify a method of analyzing the particles present in a service fluid of a device, especially an internal combustion engine, and to provide a device for performing such a method.

A basic concept of the invention is to perform the analysis method of the invention during the operation of the device (e.g., internal combustion engine), i.e., while a service fluid (e.g., motor oil) is flowing through a service fluid circuit (e.g., motor oil circuit) of the device (e.g., internal combustion engine). For this purpose, at a first branch point in the service fluid circuit of the device, a service fluid stream is branched off for analysis purposes. The service fluid stream branched off is subsequently analyzed for (damaging) particles, and by an in-line method, i.e., during the operation of the device.

Various known methods are useful for the analysis of the particles present in the branched-off service fluid stream, for example laser shadow methods, laser diffraction methods, camera-based incident light methods or filter blockage methods etc. However, many of these methods can be viably employed only over and above a certain minimum concentration of solid particles. Typically, the concentration of the solid particles present in the motor oil of internal combustion engines is so small that such methods cannot be employed directly at least.

An essential concept of the invention is that of the use of a "separation unit" which enables employment of the abovementioned methods. According to the present invention, the service fluid stream branched off from the service fluid circuit is fed to the separation unit and the separation unit is used to branch it into a first service fluid stream and a second service fluid stream, it being possible by means of the separation unit to feed a majority of the particles present in the branched-off service fluid stream to the first service fluid stream. This results in an increase in the concentration of solid particles in the first service fluid stream, which enables employment of the abovementioned analysis methods.

Accordingly, according to the invention, an electronic evaluation unit is used to evaluate at least one parameter of the particles present in the first service fluid stream. In this way, it is possible to draw conclusions as to the particles present in the overall service fluid of the device, for example in terms of their size or size distribution, number or concentration, origin etc.

It may be the case that, by means of the separation unit, more than 80% or more than 90% or more than 9.5% of the particles present in the branched-off service fluid stream are fed to the first service fluid stream. This achieves a significant increase in the particle concentration in the first service fluid stream in relation to the second service fluid stream, which is advantageous or a prerequisite for the employment of the abovementioned analysis methods or other analysis methods.

According to the invention, it is possible to use a separation unit based on the principle of centrifugal separation. For example, it is possible to use a hydrocyclone available on the market. A hydrocyclone is a purely mechanical or flow-mechanical apparatus having one fluid inlet and two fluid outlets. The branched-off service fluid stream flows into the hydrocyclone via the fluid inlet and is forced to take a circular path. In a conical section of the hydrocyclone, owing to centrifugal and vortex effects, the branched-off service fluid stream is split into the first, particle-rich service fluid stream and the second service fluid stream having a lower level of particles. The first service fluid stream flows out of the hydrocyclone via a first outlet of the hydrocyclone. The second service fluid stream flows out of the hydrocyclone via a second outlet of the hydrocyclone. The dimensions of the hydrocyclone are preferably such that the first service fluid stream is always smaller than the second service fluid stream. For example, it may be the case that the volume flow ratio of the first service fluid stream relative to the second service fluid stream is less than 1:10 or less than 1:15 or less than 1:20. For example, the first service fluid stream may be 5% of the second service fluid stream.

As already mentioned above, the first service fluid stream flowing out of the first outlet of the hydrocyclone or of the separation unit may be analyzed specifically by means of an electronic evaluation unit with regard to the solid particles present therein. A particular advantage of the present invention is considered to be that the increase in the concentration of solid particles in the first service fluid stream means that particular evaluation methods that require a minimum concentration of solid particles are applicable.

For example, an electronic evaluation unit can be used to ascertain the concentration or number of the particles present in the first service fluid stream and/or the distribution of the particle sizes of the particles present in the first service fluid stream, and/or the concentration or number of particles of particular defined particle sizes or defined particle size ranges, etc.

It is possible here, for example, to use the optical evaluation methods already mentioned above (for example laser shadow methods, laser diffraction methods, camera analysis methods etc.), or methods based on pressure differential measurements (e.g., filter blockage measurement methods).

After the evaluation by the evaluation unit, it is at least possible to introduce or return the liquid component of the first service fluid stream back into the service fluid circuit of the device.

Particles present in the first service fluid stream may be removed from the first service fluid stream by means of a filter unit downstream of the evaluation unit. For this purpose, it is possible, for example, to use a metal weave filter.

Preference is given here to using a "washable filter" (for example a metal weave filter), i.e., a filter from which the solid particles removed from the first service fluid stream can be washed out again. This is because it may be the case, according to the invention, that the particles removed by means of the filter it in the first service fluid stream are taken from the filter unit and then analyzed with regard to their chemical characteristics or their material.

By a comparison of the chemical characteristics or of the material of individual particles filtered out by means of the filter unit with the chemical compositions or materials present in a defined material database, it is then possible to determine which component(s) of the device gives rise to or could give rise to individual particles. In connection with internal combustion engines, it is thus possible to determine, for example, whether individual particles are particles from the crankcase or the manufacture of the crankcase (for example sand particles or metal turnings) or, for example, particles that originate from wear-related abrasion.

The second service fluid stream coming from the separation unit may likewise be fed back to the service fluid circuit.

When the method of the invention is employed in association with internal combustion engines, the service fluid stream may, for example, be in the range between 5 l/min and 50 l/min or in the range between 10 l/min and 40 l/min.

The invention is elucidated in detail hereinafter in connection with the drawing.

DETAILED DESCRIPTION OF THE DRAWING

Figure 1:
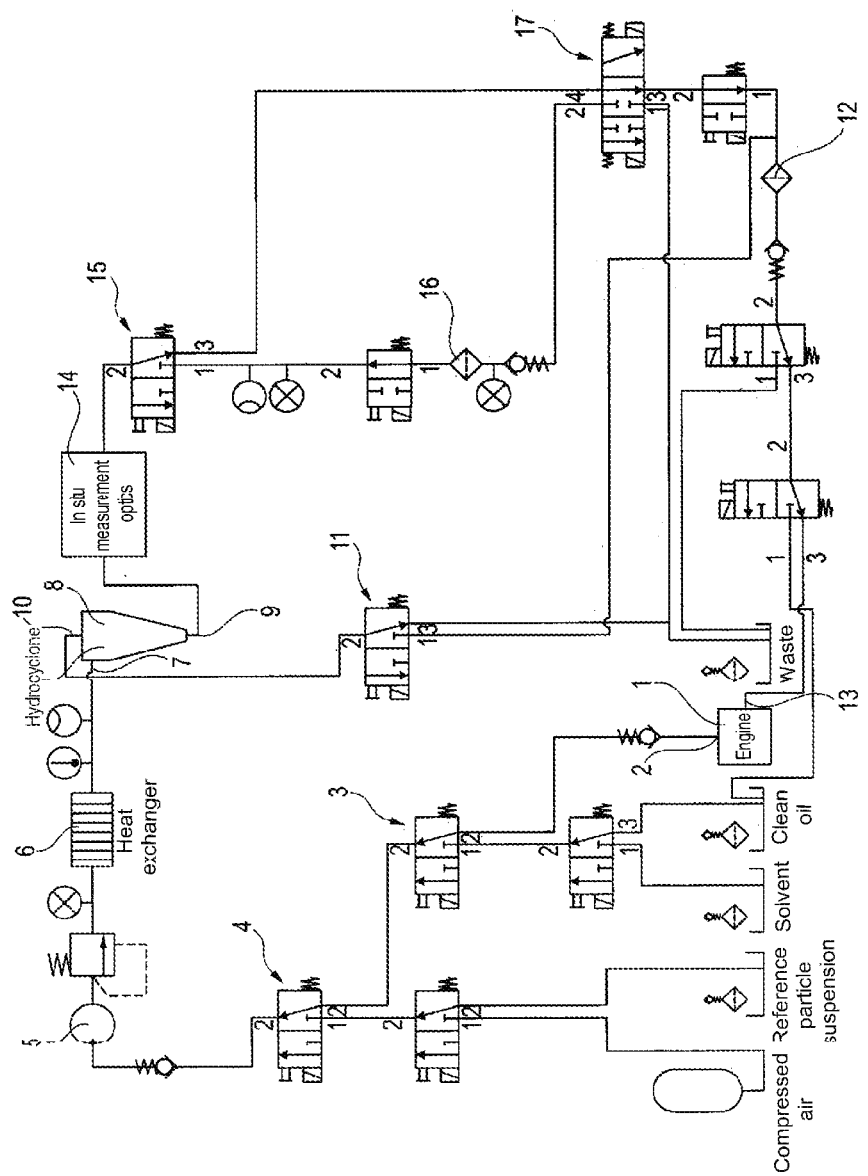
FIG. 1 shows the basic principle of the invention using a schematic circuit diagram.

An internal combustion engine 1, shown here merely in very schematic form, has, in its interior, a service fluid circuit (motor oil circuit). At a first branch point 2, service fluid (motor oil) can be branched off from the service fluid circuit (motor oil circuit) of the internal combustion engine and sucked in via valves 3, 4 by a pump 5 of the analysis device of the invention.

By means of a heat exchanger 6, the temperature of the service fluid stream branched off from the service fluid circuit of the engine can be adjusted (for example heated or cooled). Subsequently, the branched-off service fluid stream flows to an inlet 7 of a separation unit 8, which may be a gravitational separator (for example a hydrocyclone). The separation unit 8 has a first outlet 9 and a second outlet 10. The branched-off service fluid stream flowing via the inlet 7 into the separation unit 8 is branched into a first service fluid stream flowing out via the first outlet 9 and a second service fluid stream flowing out via the second outlet 10. The first service fluid stream is much smaller than the second service fluid stream. The volume flow ratio of the two service fluid streams may, for example, be less than 1:10 or less than 1:15 or less than 1:20.

The first service fluid stream flowing out via the first outlet 9, however, has a significantly greater particle concentration than the second service fluid stream flowing out via the second outlet 10. The separation unit 8 thus "steers" most of the particles flowing through the inlet 7 into the first service fluid stream. For example, more than 80% or more than 90% or more than 95% may be directed into the first service fluid stream.

The second service fluid stream flows through the second outlet 10, a valve 11, directly or indirectly through a filter 12, which may, for example, be a cellulose filter, and a further branch point 13 back into the service fluid circuit of the engine 1.

The first service fluid stream flows through the first outlet 9 to an electronic or optoelectronic evaluation unit 14. The first service fluid stream thus flows through the evaluation unit 14. As they flow through, at least one parameter of the particles present in the first service fluid stream is measured or evaluated. For example, the concentration or number of the particles present in the first service fluid stream may be ascertained. Alternatively or additionally, the distribution of the particle sizes of the particles present in the first service fluid stream may be ascertained. Alternatively or additionally, the concentration or number of particles of particular defined particle sizes or particle size ranges can be ascertained.

If "critical particles" are present in the first service fluid stream, the first service fluid stream may be directed via a valve 15 to a "washable filter" (e.g., a metal weave filter) and further via a valve 17 back into the service fluid circuit of the engine 1. Particles filtered out by means of the filter 16 may be taken from the filter 16 (for example washed out of the filter 16) and analyzed specifically with regard to their chemical characteristics or material composition. In this way, it is possible to determine, for example, which component of the engine 1 gives rise or could give rise to individual particles.

By switching over the valve 15, it is also possible to guide the first service fluid stream directly, i.e., bypassing the filter 16, via the valve 17 back into the service fluid circuit of the engine.

What is claimed is:

1. A method of analyzing particles present in a service fluid of a device, comprising the acts of:
   analyzing the particles during operation of the device wherein a service fluid flows through a service fluid circuit of the device during the analyzing;
   branching off a service fluid stream at a first branch point of the service fluid circuit;
   feeding the branched-off service fluid stream to a separation unit;
   branching the branched-off service fluid stream into a first service fluid stream and a second service fluid stream by the separation unit, wherein the first service fluid stream flows out of the separation unit via a first outlet to an evaluation unit and the second service fluid stream flows out of the separation unit via a second outlet to the service fluid circuit of the device;
   feeding a majority of particles present in the branched-off service fluid stream to the first service fluid stream by the separation unit;
   ascertaining at least one parameter of the particles fed to the first service fluid stream by the evaluation unit; and
   feeding a liquid component of the first service fluid stream, after the ascertaining, to the service fluid circuit of the device.

2. The method according to claim 1, wherein the separation unit feeds more than 80% of the particles present in the branched-off service fluid stream to the first service fluid stream.

3. The method according to claim 1, wherein the separation unit is a centrifugal separation unit.

4. The method according to claim 1, wherein the separation unit is a hydrocyclone.

5. The method according to claim 1, wherein the first service fluid stream is always smaller than the second service fluid stream.

6. The method according to claim 1, wherein a volume flow ratio of the first service fluid stream to the second service fluid stream is less than 1:10.

7. The method according to claim 1, wherein the at least one parameter is:

a. a concentration or a number of particles present in the first service fluid stream, and/or b. a distribution of particle sizes of particles present in the first service fluid stream, and/or c. a concentration or a number of particles of a defined particle size or a defined particle size range present in the first service fluid stream.

8. The method according to claim 1 further comprising the act of taking the particles fed to the first service fluid stream from the first service fluid stream by a filter unit downstream of the evaluation unit.

9. The method according to claim 8 further comprising the acts of removing the particles taken from the first service fluid stream by the filter unit from the filter unit and analyzing the removed particles with respect to a respective chemical characteristic or a material.

10. The method according to claim 9 further comprising the acts of comparing the respective chemical characteristic or the material of at least one particle with chemical compositions or materials present in a material database and ascertaining a component in the device associated with the at least one particle based on the comparing.

11. The method according to claim 1, wherein the device is an engine.

12. The method according to claim 1, wherein the service fluid is an oil.

13. The method according to claim 1, wherein the service fluid stream has a rate of flow between 5 l/min and 50 l/min.

14. A device for analyzing particles present in a service fluid of an engine, comprising:

a separation unit including:

an inlet in flow connection with a first branch point of a service fluid circuit of the engine, wherein the first branch point branches a service fluid stream off from the service fluid circuit; and a first outlet and a second outlet, wherein dimensions of the separation unit are configured such that a first service fluid stream flowing out of the separation unit via the first outlet is always smaller than a second service fluid stream flowing out of the separation unit via the second outlet and such that the first service fluid stream contains a majority of particles present in the service fluid stream, wherein the first service fluid stream flows out of the separation unit via the first outlet to an evaluation unit and the second service fluid stream flows out of the separation unit via the second outlet to the service fluid circuit of the engine;

wherein the evaluation unit ascertains at least one parameter of particles present in the first service fluid stream;

wherein a liquid component of the first service fluid stream is fed, after the evaluation unit, to the service fluid circuit of the engine.

* * * * *